United States Patent
Grant

(10) Patent No.: US 7,806,685 B1
(45) Date of Patent: Oct. 5, 2010

(54) DENTAL IMPLANT APPARATUS AND METHOD UTILIZING A BASE DIRECTLY ATTACHED TO THE BONE IN A JAW

(76) Inventor: James C. Grant, 8 Pine Rd., Colorado Springs, CO (US) 80906

( * ) Notice: Subject to any disclaimer, the term of this patent is extended or adjusted under 35 U.S.C. 154(b) by 51 days.

(21) Appl. No.: 12/074,524

(22) Filed: Mar. 4, 2008

(51) Int. Cl.
*A61C 8/00* (2006.01)

(52) U.S. Cl. ......................................................... 433/14

(58) Field of Classification Search ......... 433/172–176, 433/201.1, 202.1, 215, 220, 221
See application file for complete search history.

(56) References Cited

U.S. PATENT DOCUMENTS

| | | | |
|---|---|---|---|
| 4,086,701 A | | 5/1978 | Kawahara et al. |
| 5,040,982 A | | 8/1991 | Stefan-Dogar |
| 5,297,963 A | | 3/1994 | Dafatry |
| 5,513,989 A | * | 5/1996 | Crisio .......................... 433/176 |
| 5,564,925 A | * | 10/1996 | Shampanier ................. 433/173 |
| 5,591,029 A | | 1/1997 | Zuest |
| 5,810,592 A | | 9/1998 | Daftary |
| 6,068,479 A | * | 5/2000 | Kwan .......................... 433/173 |
| 6,168,436 B1 | | 1/2001 | O'Brien |
| 6,250,922 B1 | * | 6/2001 | Bassett et al. ................ 433/172 |
| 6,287,117 B1 | | 9/2001 | Niznick |
| 6,537,069 B1 | * | 3/2003 | Simmons, Jr. ................ 433/173 |
| 2004/0265781 A1 | | 12/2004 | Coatoam |
| 2006/0014120 A1 | | 1/2006 | Sapian |
| 2008/0118892 A1 | * | 5/2008 | Adams ........................ 433/174 |

* cited by examiner

*Primary Examiner*—Cris L Rodriguez
*Assistant Examiner*—Heidi M Eide
(74) *Attorney, Agent, or Firm*—Townsend and Townsend and Crew LLP

(57) ABSTRACT

A dental implant system in one embodiment is constructed of a base member that is to be embedded within a patient's jawbone. This base member has a central opening that tapers inward from a top surface to a bottom surface. The system also includes an implant screw having a head and a threaded end which passes through the central opening of the base member and into the patient's jawbone. The head has a tapered section to seat within the tapered opening of the base member. In this way, the base member is secured to the jawbone while the base member is embedded within the patient's jawbone. A crown is provided to be coupled to the implant screw.

9 Claims, 3 Drawing Sheets

DENTAL IMPLANT APPARATUS AND METHOD UTILIZING A BASE DIRECTLY ATTACHED TO THE BONE IN A JAW

FIELD OF THE INVENTION

This invention relates to an improved method for implanting a tooth prostheses. More particularly the method utilizes an enlarged, generally rectangular base for the crown portion of the tooth prostheses. The enlarged, generally rectangular base facilitates use of the crown portion of the tooth prostheses having an enlarged bottom portion. The enlarged, generally rectangular base not only better distributes load on the jawbone, but additionally substantially reduces the problem of food impaction by reducing the size of the embrasures, between the crown portion of the implant and the adjacent teeth on opposite sides thereof.

BACKGROUND OF THE INVENTION

Implants are now the most popular means of replacing a lost tooth. Due to their relatively low maintenance and durability people are increasingly preferring implants to bridges. None the less, there is a largely undocumented body of complaints in the prosthetic manufacturer's literature, which is voiced to front line dentists about implants, by their patients. These complaints generally are about food impacting and accumulating around and beneath the crown portion of the implant in the enlarged embrasure between the implant and the adjacent teeth.

In current practice after a tooth has been removed, first i) an upright pilot hole which is centered in the opening left by the removed tooth, is drilled in the jaw, and then ii) a self-tapping retaining screw, having an upper internally threaded opening therein, is turned into the pilot hole, beneath the removed tooth. The top side portion of the retaining screw comprises a platform to which a crown prosthetic portion is subsequently attached thereon, utilizing the internally threaded opening in the top portion of the retaining screw. iii) After the retaining screw is inserted in the jawbone the gum is sutured closely around the top portion of the retaining screw. iv) Finally, the upper crown portion of the implant is cast to fit the opening between the adjacent teeth. The peripheral sides of the crown portion of the implant taper from the large generally rectangular upper crown portion to a base diameter which corresponds to the platform diameter of the retaining screw. Generally the upper crown portion is rectangular; generally the lower crown is round; and generally the diameter of the base portion is less than one half of the length of the rectangular portion.

This is the essence of the problem of impacting and accumulating trapped food. A tooth which was generally rectangular from top to bottom, has been replaced by a prostheses having a custom fitted generally rectangular upper crown portion, and a generally round bottom portion, sized not to even approximately fit the opening between the adjacent teeth, but rather extremely narrowed to seat on the top face of the retaining screw. The embrasures, the spaces between the implant and the adjoining teeth, has been multiply enlarged. Food packs therein, and it must be constantly, and inconveniently, removed to prevent gingival inflammation and gum infection. Patients have little option but to carry floss or a toothpick and remove debris after every time they eat.

OBJECTS OF THE INVENTION

It is an object of this invention to disclose an apparatus and method of implanting a tooth prostheses utilizing an enlarged, generally rectangular base portion. It is an object of this invention to disclose an apparatus and method of minimizing the embrasures between an implanted tooth prostheses and the adjacent teeth so that the problem of increased trapped food, gingival inflammation and gum infection is not associated with a tooth implant. It is yet a further object of this invention to disclose an apparatus and method of a tooth implant which will provide better stability and stress distribution on the jawbone. It is yet a further object of this invention to eliminate the necessity of a dental implant patient carrying dental floss or a toothpick and immediately remove debris from under and around the implant after every time they eat. It is a final object of this invention to disclose an apparatus and method of implanting a tooth which will provide a more natural looking tooth which will be much more serviceable with dramatically reduced maintenance.

One aspect of this invention provides for a tooth implant comprising: i) a crown portion having a lower portion adapted for seating and connection; ii) a base having an upper portion adapted to matably receive the crown portion, a lower portion adapted to seat directly on the bone of one of the jaws, said base having an upright opening therethrough; and, iii) a base attachment screw having a head adapted to be seat on and around the upright opening, and a threaded end portion for screwable reception in the jaw to thereby anchor the base thereon. The base of the implant is enlarged to better distribute the load on the jaw and thereby additionally allow said crown portion to have more upright peripheral sidewalls, so that embrasures between the bottom portion of the crown portion are thereby substantially reduced, and so that both food impaction and collection therein is also substantially reduced.

In a preferred aspect of this invention the base is generally rectangular and non-rotatable. The top portion of the base and the bottom side portion of the crown are matingly configured to ensure proper and non-rotatable alignment of the crown portion on the base.

Another aspect of the invention provides for a general method of implanting a tooth prostheses in a jawbone comprises the following steps: i) providing a tooth implant as most generally described above; ii) drilling a pilot hole, sized to accommodate the internal diameter of the base attachment screw, said hole laterally centered in the jaw between adjacent teeth in an open space; iii) removing sufficient gum to allow the base to seat directly on the bone of the jaw, and thereafter positioning the threaded end portion of the base attachment screw through the upright opening in the base and screwing said screw into the bone of the jaw thereby attaching the base to the jaw; iv) thereafter positioning, fitting and maintaining the removed gum peripherally around the base attached to the jaw; v) molding a crown portion having a bottom portion sized to fit on the base and a top portion sized appropriately to fill the open space between the adjacent teeth; and, vi) finally attaching the molded crown portion to the base anchored on the jaw. The base of the implant is enlarged to better distribute the load on the jaw, so that embrasures between the bottom portion of the crown portion and adjacent teeth are thereby reduced, and so that both food impaction and collection therein is minimal.

Various other objects, advantages and features of this invention will become apparent to those skilled in the art from the following description in conjunction with the accompanying drawings.

FIGURES OF THE INVENTION

Figure 1:
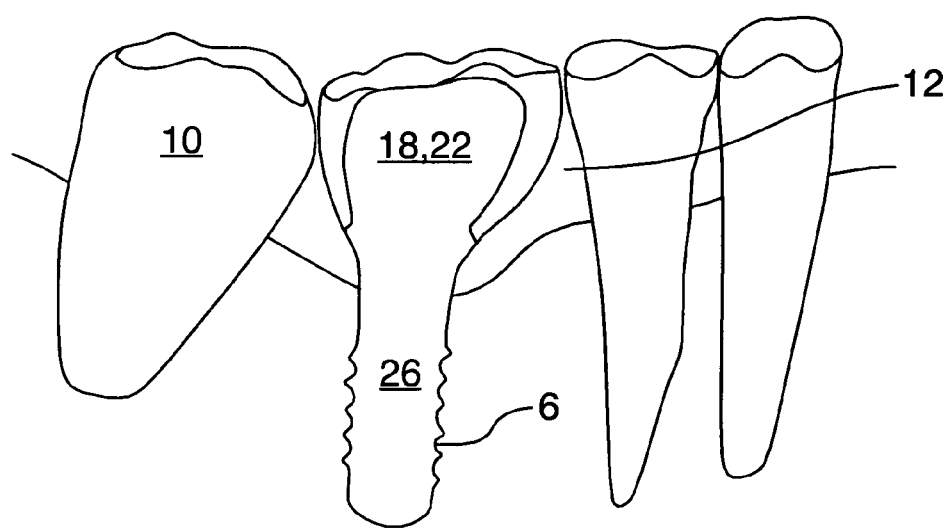
FIG. 1 is an elevational view of a conventional implant comprising a crown portion mounted on a self-tapping retaining screw anchored in the jaw.

The following is a discussion and description of the preferred specific embodiments of this invention, such being made with reference to the drawings, wherein the same reference numerals are used to indicate the same or similar parts and/or structure. It should be noted that such discussion and description is not meant to unduly limit the scope of the invention.

DESCRIPTION OF THE INVENTION

Figure 2:
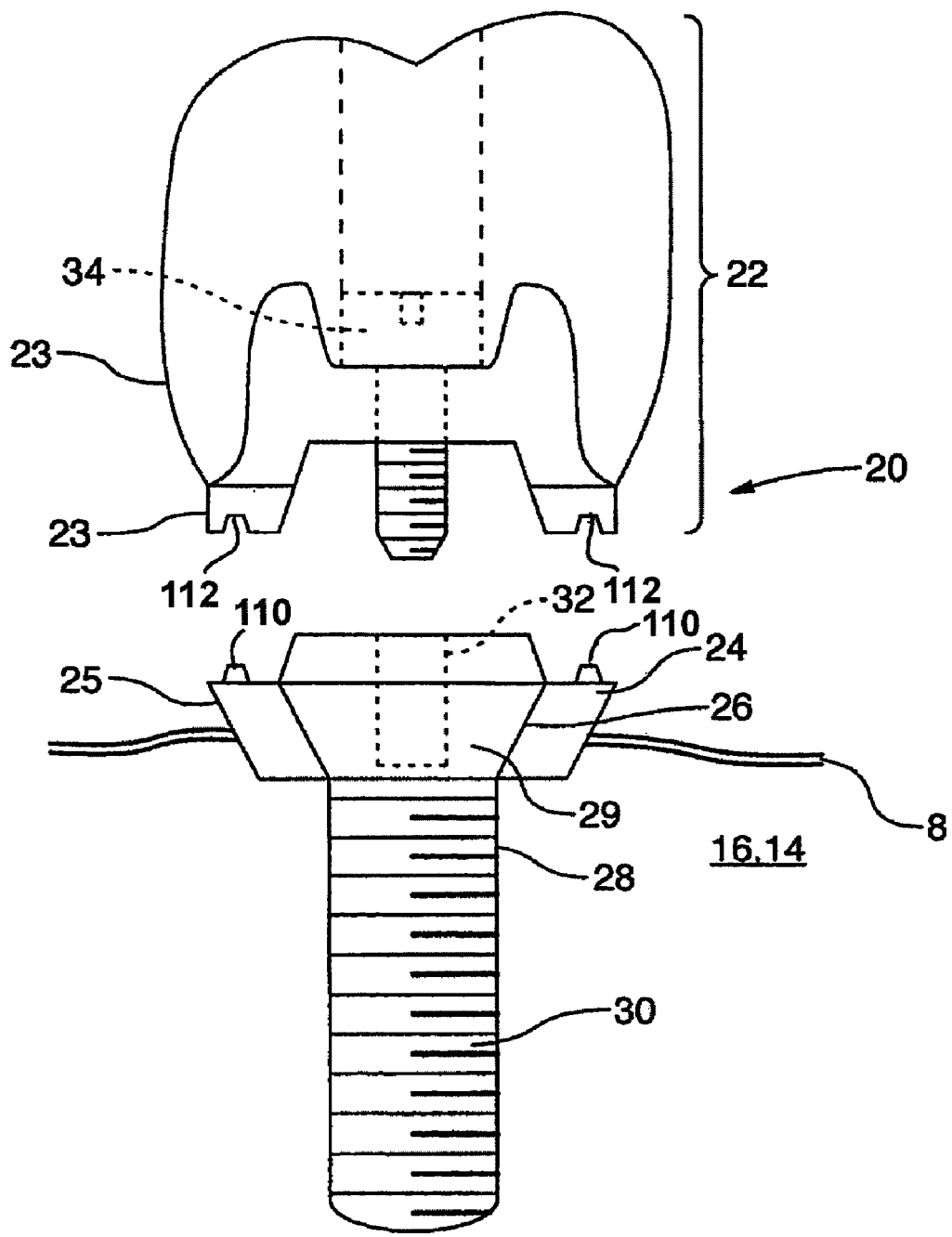
FIG. 2 is an elevational view of an implant having an enlarged base seated directly on the jawbone.
Figure 3:
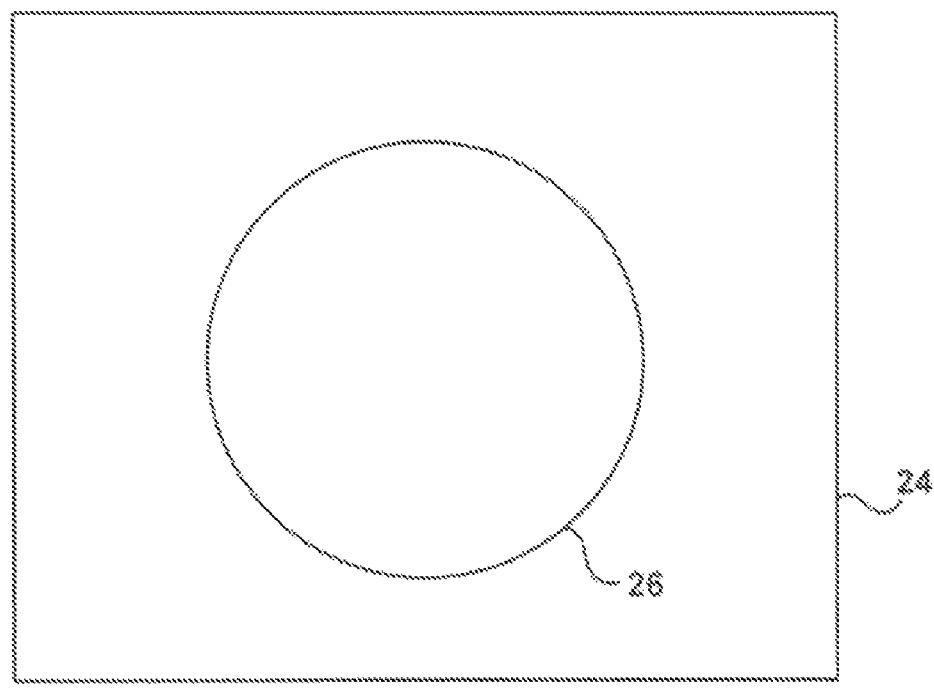
FIG. 3 is a top view of the base of FIG. 2.

Turning now to the drawings and more particularly to FIG. 1 we have an elevational view of a conventional implant 18 comprising a crown portion 22 mounted on a self-tapping retaining screw 26 anchored in the jawbone 16. FIG. 2 is an elevational view of an improved implant or prostheses 20 having an enlarged base 24 seated directly on the jawbone 16. Most generally the improved tooth implant 20 comprises: i) a crown portion 22 having a lower portion 23 adapted for seating and connection; ii) a base 24 having an upper portion adapted to matably receive the crown portion 22, a lower portion adapted to seat directly on the bone of one of the jaws 14, said base 24 having an upright opening 26 therethrough; and a base attachment screw 28 having a head 29 adapted to be seat on and around the upright opening 26, and a threaded end portion 30 for screwable reception in the jaw 14 to thereby anchor the base 24 thereon. The base 24 of the implant 20 is enlarged to better distribute load on the jaw 14 and thereby additionally allow said crown portion 22 to have more upright peripheral sidewalls 23, so that embrasures 12 between the bottom portion of the crown portion an adjacent teeth 10 are thereby substantially reduced, and so that both food impaction and collection therein is also substantially reduced. Most preferably the base 24 is generally rectangular (see FIG. 3) and non-rotatable.

Within this specification "jaw" 14 is intended and defined to include either the upper jaw or the lower jaw. Similarly, within this specification "bone" 16 is intended and defined to include either the maxilla or the mandible.

If the base 24 is sized generally similarly to the bottom portion of a removed tooth (not shown) then the embrasures 12 on opposite sides of the implanted crown portion 22 will not be enlarged. The base 24 may be further enlarged to maximally minimize the embrasures 12 between the implant 20 and adjacent teeth 10.

In a preferred embodiment of the invention the base 24 has a sloping peripheral sidewall 25 and wherein the bottom side portion is smaller in area than the top side portion thereof. The bottom side portion of the base 24 may be embedded within the bone 14 of the jaw 16. Alternatively, if bone 14 strength is an issue, the bottom side portion of the base 24 may be generally fitted to the vertical curvature of the bone 14 of the jaw 16.

In another preferred embodiment of the invention the peripheral sidewall 25 of the base 24 is coated/roughened to facilitate gum 8 adhesion thereto. Most preferably the upper portion of the base attachment screw 28 comprises an internally threaded hole 32 for reception of a crown attachment bolt 34. It is also contemplated that the top portion of the base 24 and the bottom side portion of the crown 22 are matingly configured with matable features 110 and 112 to ensure proper and non-rotatable alignment of the crown portion 22 on the base 24.

Most generally, a method of implanting a tooth implant or prostheses 20 in a jaw 16 comprises the following steps: i) providing a tooth implant 20 as most generally described above; ii) drilling a pilot hole 6, sized to accommodate the internal diameter of the base attachment screw 28, said hole 6 laterally centered in the jaw 16 between adjacent teeth 10 in an open space left by a removed tooth (not shown); iii) removing sufficient gum 8 to allow the base 24 to seat directly on the bone 14 of the jaw 16, and thereafter positioning the threaded end portion 30 of the base attachment screw 28 through the upright opening 26 in the base 24 and screwing said screw 28 into the bone 14 of the jaw 16 thereby attaching the base 24 to the jaw 16; iv) thereafter positioning, fitting and maintaining the removed gum 8 peripherally around the base 24 attached to the jaw 16; v) molding a crown portion 22 having a bottom portion sized to fit on the base 24 and having a top portion sized appropriately to fill the open space between the adjacent teeth 10; and, vi) finally attaching the molded crown portion 22 to the base 24 anchored on the jaw 16. The base 24 of the implant 20 is enlarged to better distribute load on the jaw 16, so that embrasures 12 between the bottom portion of the crown portion 22 and adjacent teeth 10 are thereby reduced, and so that both food impaction and collection therein is minimal. This most general method may be detailed with the apparatus limitations specified above under the most general description of the tooth implant 20.

While the invention has been described with preferred specific embodiments thereof, it will be understood that this description is intended to illustrate and not to limit the scope of the invention, which is defined by the following claims.

I claim:

1. A dental implant system comprising:
    a base member that is adapted to be embedded within a patient's jawbone at a treatment site, wherein the base member has a generally flat top side, a generally flat bottom side, and a central opening that is geometrically centrally located within the base member, wherein the central opening tapers inward with a constant taper from the top surface to the bottom surface, wherein the top side further includes at least one matable feature that is configured to mate with a corresponding feature on a crown to ensure non-rotatable alignment of the crown with the base member, and wherein the base member has an outer periphery that tapers with a straight taper inward from the top surface to the bottom surface such that the top surface is greater in surface area than the bottom surface;
    an implant screw comprising a head and a threaded end, wherein the threaded end is adapted to pass through the central opening of the base member and into the patient's jawbone, and wherein the head has a tapered section that is adapted to be seated within the tapered opening of the base member after the threaded end is screwed into the patient's jawbone, with the implant screw securing the base member to the jawbone while the base member is embedded within the patient's jawbone, wherein the head of the implant screw includes a threaded hole in the head that extends downward through the tapered section; and
    a crown that is adapted to be mounted to the head of the implant screw via a screw that passes into the threaded hole in the head of the implant screw, wherein the crown includes a corresponding matable feature that mates with the base member, wherein the matable feature of the base member comprises a projection adjacent the outer periphery that projects upward from the top side of the base member a distance that is below the head of the implant screw, and wherein the matable feature of the crown comprises a recess on a bottom end of the crown.

2. A system as in claim 1, wherein the outer periphery of the base member is roughened.

3. A system as in claim 1, wherein the base member is generally rectangular in geometry.

4. A method for securing a dental implant within a patient's jawbone, the method comprising:
   removing a portion of the patient's gum at a treatment site sufficient to expose the patient's jawbone;
   positioning a base member at the treatment site such that the base member is embedded within the patient's jawbone at the treatment site, wherein the base member has a generally flat top side, a generally flat bottom side, and a central opening, wherein the central opening tapers inward from the top surface to the bottom surface with a constant taper, wherein the base member is embedded within the patient's jawbone such that the bottom surface contacts the jawbone when embedded within the jawbone, wherein the top side further includes at least one matable feature that is configured to mate with a corresponding feature on a crown to ensure non-rotatable alignment of the crown with the base member, and wherein the base member has an outer periphery that tapers with a straight taper inward from the top surface to the bottom surface such that the top surface is greater in surface area than the bottom surface;
   inserting an implant screw through the opening, wherein the implant screw has a head with a tapered section and a threaded end, wherein the head of the implant screw includes a threaded hole in the head that extends downward through the tapered section; and
   turning the screw to secure the threaded end within the jawbone and to seat the head of the implant screw within the tapered opening of the base member; and
   attaching a crown to the implant screw by passing a screw into the threaded hole in the head of the implant screw, wherein the crown includes a corresponding matable feature that mates with the feature on the base member to non-rotationally secure the crown to the base member, wherein the matable feature of the base member comprises a projection adjacent the outer periphery that projects upward from the top side of the base member a distance that is below the head of the implant screw, wherein the matable feature of the crown comprises a recess on a bottom end of the crown, and wherein the crown is attached to the implant screw such that the projection extends in to the recess.

5. A method as in claim 4, wherein the treatment site is where a tooth previously existed.

6. A method as in claim 5, wherein the base member is sized to be generally the same size as the removed tooth.

7. A method as in claim 4, wherein the base member is generally rectangular in geometry.

8. A method as in claim 4, wherein the outer periphery of the base member is roughened.

9. A dental implant system comprising:
   a base member that is adapted to be embedded within a patient's jawbone at a treatment site, wherein the base member has a generally flat top side, a generally flat bottom side, and a central opening, wherein the central opening tapers inward with a constant taper from the top surface to the bottom surface, wherein the top side further includes at least one matable feature that is configured to mate with a corresponding feature on a crown to ensure non-rotatable alignment of the crown with the base member, and wherein the base member has an outer periphery that tapers with a straight taper inward from the top surface to the bottom surface such that the top surface is greater in surface area than the bottom surface, wherein the matable feature of the base member comprises a projection adjacent the outer periphery that projects upward from the top side of the base member a distance that is below the head of the implant screw and is configured to fit within a recess on a bottom end of the crown;
   an implant screw comprising a head and a threaded end, wherein the threaded end is adapted to pass through the central opening of the base member and into the patient's jawbone, and wherein the head has a tapered section that is adapted to be seated within the tapered opening of the base member after the threaded end is screwed into the patient's jawbone, with the implant screw securing the base member to the jawbone while the base member is embedded within the patient's jawbone, wherein the head of the implant screw includes a threaded hole in the head that extends downward through the tapered section;
   wherein the outer periphery of the base member is roughened; and
   wherein the base member is generally rectangular in geometry.

* * * * *